(12) United States Patent
Cho et al.

(10) Patent No.: US 9,359,382 B2
(45) Date of Patent: Jun. 7, 2016

(54) β-KETOIMINE LIGAND, METHOD OF PREPARING THE SAME, METAL COMPLEX COMPRISING THE SAME AND METHOD OF FORMING THIN FILM USING THE SAME

(71) Applicant: SAMSUNG ELECTRONICS CO., LTD., Suwon-si, Gyeonggi-do (KR)

(72) Inventors: Youn-Joung Cho, Suwon-si (KR); Senji Wada, Tokyo (JP); Jung-Sik Choi, Seongnam-si (KR); Jin-Seo Lee, Anyang-si (KR); Atsushi Sakurai, Tokyo (JP); Kyoo-Chul Cho, Yongin-si (KR); Atsuya Yoshinaka, Tokyo (JP); Haruyoshi Sato, Tokyo (JP); Junji Ueyama, Tokyo (JP); Tomoharu Yoshino, Tokyo (JP); Masako Shimizu, Tokyo (JP)

(73) Assignees: SAMSUNG ELECTRONICS CO., LTD., Suwon-si, Gyeonggi-do (KR); ADEKA CORPORATION, Tokyo (JP)

( * ) Notice: Subject to any disclaimer, the term of this patent is extended or adjusted under 35 U.S.C. 154(b) by 50 days.

(21) Appl. No.: 14/317,102

(22) Filed: Jun. 27, 2014

(65) Prior Publication Data

US 2014/0309456 A1    Oct. 16, 2014

Related U.S. Application Data

(62) Division of application No. 13/435,760, filed on Mar. 30, 2012, now abandoned.

(30) Foreign Application Priority Data

Apr. 1, 2011 (KR) .................. 10-2011-0030224

(51) Int. Cl.
| | |
|---|---|
| *C23C 16/06* | (2006.01) |
| *C07F 3/00* | (2006.01) |
| *C07C 249/02* | (2006.01) |
| *C07C 251/08* | (2006.01) |
| *C23C 16/18* | (2006.01) |

(52) U.S. Cl.
CPC ............... *C07F 3/003* (2013.01); *C07C 249/02* (2013.01); *C07C 251/08* (2013.01); *C23C 16/18* (2013.01)

(58) Field of Classification Search
None
See application file for complete search history.

(56) References Cited

U.S. PATENT DOCUMENTS

| | | | |
|---|---|---|---|
| 6,099,903 A | 8/2000 | Kaloyeros et al. | |
| 2007/0248754 A1 | 10/2007 | Lei et al. | |

FOREIGN PATENT DOCUMENTS

| | | | |
|---|---|---|---|
| JP | 2010-111672 A | | 5/2010 |
| JP | 2011-195474 | * | 10/2011 |
| KR | 1993-0001340 B1 | | 2/1993 |

OTHER PUBLICATIONS

Yoshinaka JP2011-195474 Oct. 2011 English abstract.*

* cited by examiner

*Primary Examiner* — Joseph Miller, Jr.
(74) *Attorney, Agent, or Firm* — Lee & Morse, P.C.

(57) ABSTRACT

The β-ketoimine ligand is represented by the following formula 1:

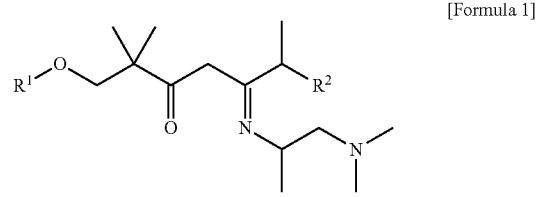

[Formula 1]

wherein R1 and R2 are each independently a C1-C5 alkyl group. A metal complex compound includes the β-ketoimine ligand. A method of forming the β-ketoimine ligand and a method of forming a thin film using the metal complex compound including β-ketoimine ligand are provided.

2 Claims, 6 Drawing Sheets

β-KETOIMINE LIGAND, METHOD OF PREPARING THE SAME, METAL COMPLEX COMPRISING THE SAME AND METHOD OF FORMING THIN FILM USING THE SAME

CROSS-REFERENCE TO RELATED APPLICATIONS

This is a divisional application based on pending application Ser. No. 13/435,760, filed Mar. 30, 2012, the entire contents of which is hereby incorporated by reference.

This application is based on and claims priority from Korean Patent Application No. 10-2011-0030224, filed on Apr. 1, 2011 in the Korean Intellectual Property Office, the disclosure of which is incorporated herein in its entirety by reference.

BACKGROUND

1. Field

Embodiments relate to a β-ketoimine ligand, a method of preparing the same, a metal complex compound comprising the same and a method of forming a thin film using the same.

2. Description of the Related Art

Among thin film fabrication techniques, a metal organic chemical vapor deposition (MOCVD) process is used to fabricate various thin films. The MOCVD is advantageous in that it uses a relatively simple system, provides uniform step coverage, makes it easy to control components and is suitable for the fabrication of large-area thin films. In order to fabricate thin films using the MOCVD process, the development of precursors to be used in this process is desirable.

SUMMARY

According to an embodiment, there is provided a β-ketoimine compound represented by the following Formula 1:

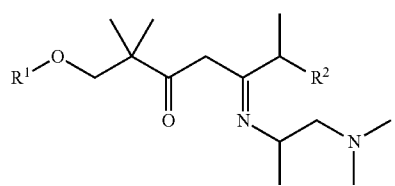

[Formula 1]

wherein $R^1$ and $R^2$ are each independently a $C_1$-$C_5$ alkyl group.

$R^1$ and $R^2$ may each independently be a methyl group or an ethyl group.

According to an embodiment, there is provided a method for preparing a β-ketoimine compound, the method including synthesizing an ether ester by converting a hydroxyl group of a hydroxypivalic acid ester into an alkoxy group using an alkylating agent, synthesizing a β-diketone compound by allowing the ether ester to react with a ketone compound, and synthesizing the β-ketoimine ligand by allowing the β-diketone compound to react with 1-dimethylamino-2-propylamine.

The β-ketoimine compound may be represented by the following Formula 1:

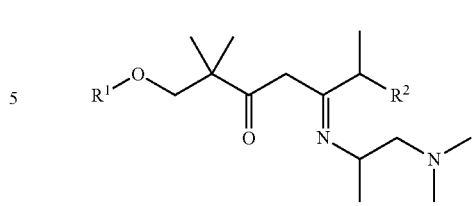

[Formula 1]

wherein $R^1$ and $R^2$ are each independently a $C_1$-$C_5$ alkyl group.

The hydroxypivalic acid ester may be hydroxypivalic acid methyl ester.

The ether ester may be represented by the following formula:

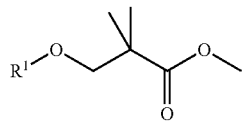

wherein $R^1$ is a $C_1$-$C_5$ alkyl group.

The ketone compound may be represented by the following formula:

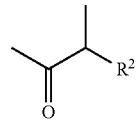

wherein $R^2$ is a $C_1$-$C_5$ alkyl group.

The alkylating agent may be p-toluenesulfonic acid methyl ester or p-toluenesulfonic acid ethyl ester.

According to an embodiment, there is provided a metal complex compound represented by the following Formula 3:

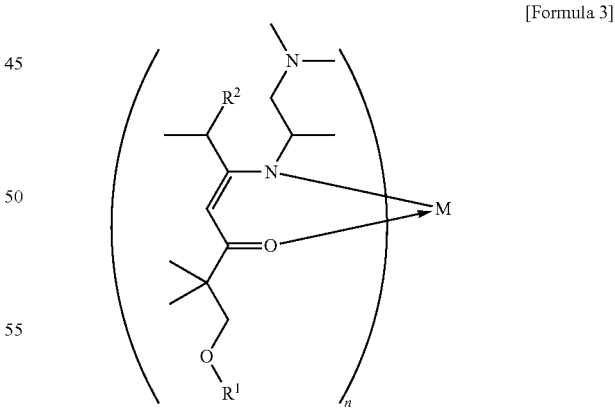

[Formula 3]

wherein $R^1$ and $R^2$ are each independently a $C_1$-$C_5$ alkyl group, M represents a metal, and n is an integer ranging from 1 to 5.

The metal may be strontium.

$R^1$ and $R^2$ may each independently be a methyl group or an ethyl group.

The metal complex compound may be prepared by allowing a β-ketoimine ligand represented by the following Formula 1 to react with a group I or II metal or a metal raw material including the group I or II metal:

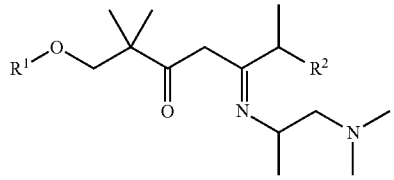

[Formula 1]

wherein $R^1$ and $R^2$ are each independently a $C_1$-$C_5$ alkyl group.

According to an embodiment, there is provided a metal precursor for forming a metal thin film, the metal precursor including a metal complex compound represented by the following Formula 3:

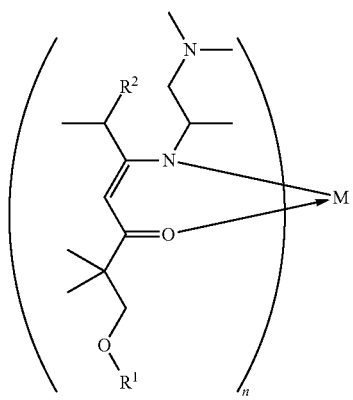

[Formula 3]

wherein $R^1$ and $R^2$ are each independently a $C_1$-$C_5$ alkyl group, M represents a metal, and n is an integer ranging from 1 to 5.

The metal may be strontium.

According to an embodiment, there is provided a method for forming a metal thin film on a workpiece, the method including vaporizing a metal precursor including the metal complex compound, and supplying the vaporized metal precursor to form a metal thin film on the workpiece.

The method may further include supplying a reactive gas simultaneously or sequentially with the supplying of the vaporized metal precursor. The forming of the metal thin film on the workpiece may include allowing the reactive gas to react with the vaporized metal precursor.

The reactive gas may include one or more of water, oxygen, ozone and hydrogen peroxide.

According to an embodiment, there is provided a method for forming a metal thin film on a workpiece, the method including supplying a first raw material including a metal complex compound including a metal and a β-ketoimine ligand represented by the following Formula 1 coordinated to the metal, and a second raw material including a reactive gas, and allowing the first raw material and the second raw material to react with each other, thereby forming the metal thin film on the workpiece:

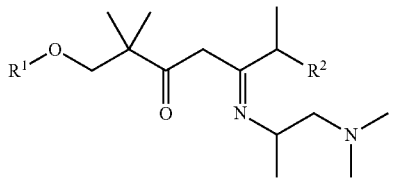

[Formula 1]

wherein $R^1$ and $R^2$ are each independently a $C_1$-$C_5$ alkyl group.

$R^1$ and $R^2$ may each independently be a methyl group or an ethyl group, and the metal may be strontium.

The method may further include supplying a third raw material including a metal precursor containing barium or titanium.

BRIEF DESCRIPTION OF THE DRAWINGS

Features will become apparent to those of ordinary skill in the art by describing in detail exemplary embodiments with reference to the attached drawings in which.

DETAILED DESCRIPTION

Figure 1:
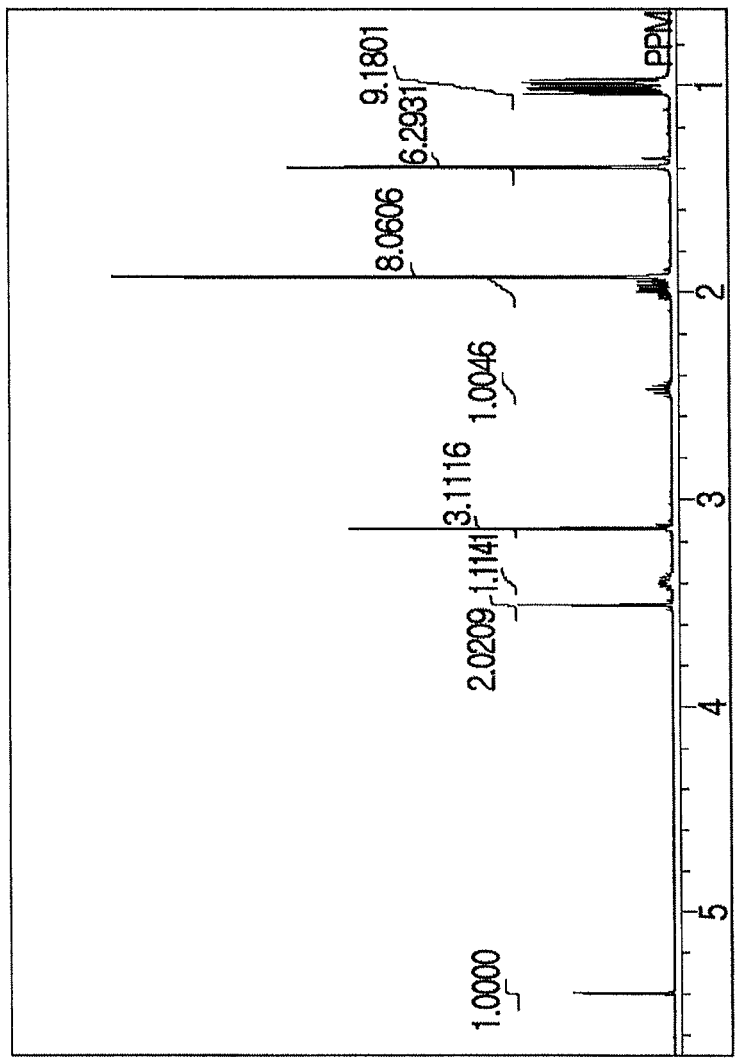
FIG. 1 illustrates the $^1$H-NMR spectrum of the β-ligand prepared in Synthesis Example 1.

Example embodiments will now be described more fully hereinafter; however, they may be embodied in different forms and should not be construed as limited to the embodiments set forth herein. Rather, these embodiments are provided so that this disclosure will be thorough and complete, and will fully convey the scope of the invention to those skilled in the art.

A β-ketoimine ligand according to an embodiment may be represented by the following Formula 1:

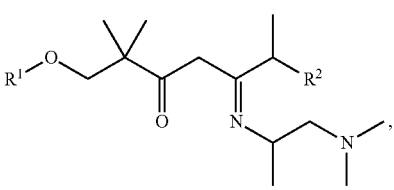

[Formula 1]

wherein $R^1$ and $R^2$ may each independently be a $C_1$-$C_5$ alkyl group.

$R^1$ and $R^2$ may be the same or different from each other. For example, $R^1$ and $R^2$ may independently be a methyl or ethyl group. The β-ketoimine ligand represented by Formula 1 may include a methyl group bound to position 1 (C1) of the N branched-chain and a dimethylamino group bound to the end of the N branched-chain. One end of the main chain of the β-ketoimine ligand represented by Formula 1 may be isopropyl group or sec-butyl group, and the other end may be 2-(methoxymethyl)propan-2-yl or 2-(ethoxymethyl)propan-2-yl.

The β-ketoimine ligand according to an embodiment may form a metal complex compound by coordination to a central metal atom. Particularly, due to this structure, the β-ketoimine ligand according to an embodiment may provide sufficient volatility, a low melting point and excellent thermal stability and organic solvent solubility to a metal complex compound whose central metal is a group II element. As an example, the central metal may be strontium.

The β-ketoimine ligand according to an embodiment is tautomeric and is in equilibrium with corresponding enamine as shown in the following Formula 2:

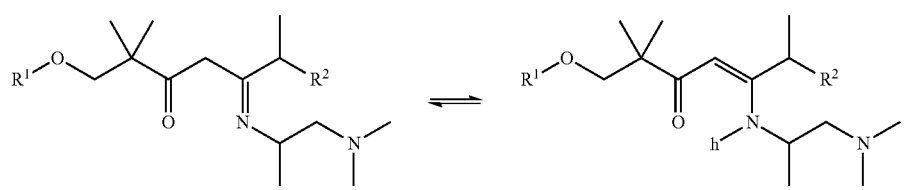

[Formula 2]

Hereinafter, a method for preparing the β-ketoimine compound according to an embodiment will be described with reference to Reaction Schemes 1 to 3 below. Reaction Schemes 1 to 3 schematically show a process for preparing the β-ketoimine compound.

Referring to Reaction Scheme 1, an alkylating agent is added to a hydroxypivalic acid ester to synthesize an intermediate ether ester compound.

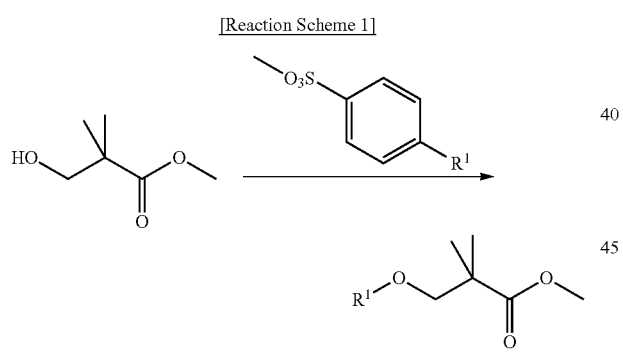

[Reaction Scheme 1]

wherein $R^1$ may be a $C_1$-$C_5$ alkyl group, and particularly, may be a methyl or ethyl group.

In this process, the hydroxyl group of the hydroxypivalic acid ester is converted to an alkoxy group ($R^1$ bound to oxygen), for example, a methoxy or ethoxy group, by the alkylating agent. Specifically, the hydroxypivalic acid ester used herein may be hydroxypivalic acid methyl ester. The alkylating agent may be an organic compound that alkylates a molecule, and examples thereof include nitrogen mustard compounds, nitrosourea compounds, aziridine compounds, methanesulfonic acid esters, platinum complex compounds, and alkylbenzene sulfonates. Particularly, the alkylating agent may be p-toluenesulfonic acid or p-toluenesulfonic acid ethyl ester.

Referring to Reaction Scheme 2, the ether ester compound is then allowed to react with a ketone compound to synthesize a β-diketone compound.

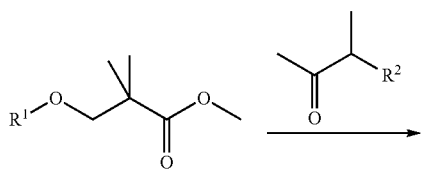

[Reaction Scheme 2]

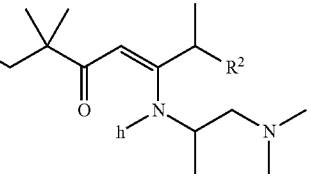

-continued

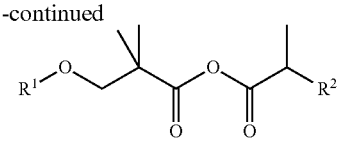

wherein $R^2$ may be a $C_1$-$C_5$ alkyl group, and particularly, a methyl or ethyl group.

When the ether ester compound produced in Reaction Scheme 1 is allowed to react with the ketone compound, two ketone groups are produced in place of the ester group so that the β-diketone compound is produced. Particularly, the ketone compound may be isopropylketone or methylpentanone.

Referring to Reaction Scheme 3, the resulting reaction product β-diketone compound is allowed to react with 1-dimethylamino-2-propylamine.

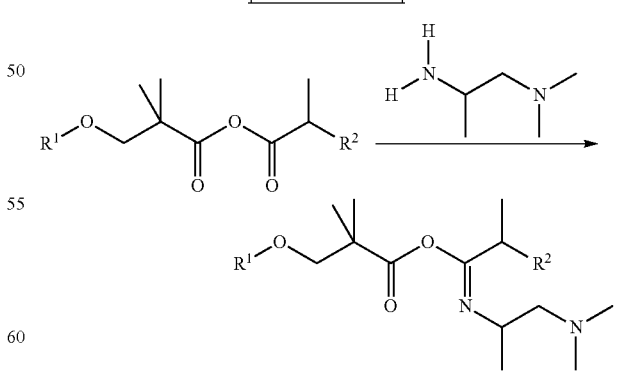

[Reaction Scheme 3]

wherein $R^1$ and $R^2$ may each independently be a $C_1$-$C_5$ alkyl group, and particularly a methyl or ethyl group.

According to the above-described process, the β-ketoimine compound, including a dimethylamino group at the N branched-chain and a 2-(methoxymethyl)propan-2-yl or 2-(ethoxymethyl)propan-2-yl group at one side of the main chain, may be prepared.

Hereinafter, a metal complex compound according to an embodiment will be described. A metal complex compound according to an embodiment includes the above-described β-ketoimine compound.

The metal complex compound according to an embodiment includes the β-ketoimine compound coordinated as a ligand to a central metal atom. The metal complex compound may be a chelate form including at least one β-ketoimine ligand coordinated thereto. The metal complex compound may include the β-ketoimine ligand coordinated to a central metal atom. Accordingly, the metal complex compound may have good volatility, excellent thermal stability and excellent solubility in an organic solvent, due to the structure of the β-ketoimine ligand.

The metal complex compound according to an embodiment may be represented by the following Formula 3:

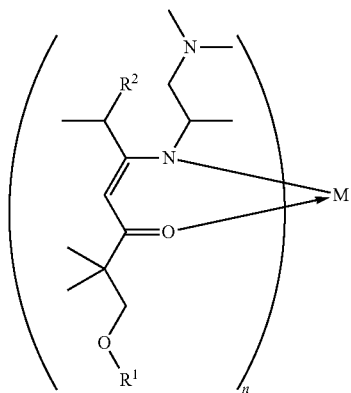

[Formula 3]

wherein $R^1$ and $R^2$ may each independently be an alkyl group having 1 to 5 carbon atoms, M represents a central metal atom, n is the number of ligands coordinated to the central metal atom (M) and represents an integer ranging from 1 to 5. $R^1$ and $R^2$ may be the same or different from each other, and may each independently be a methyl or ethyl group. The arrow indicates an optional bond between the oxygen atom and the central metal atom.

Examples of the central metal atom represented by M include group I elements, including lithium (Li), sodium (Na), potassium (K), rubidium (Rb), and cesium (Cs); group II elements, including beryllium (Be), magnesium (Mg), calcium (Ca), barium (Ba), and strontium (Sr); group III elements, including scandium (Sc), yttrium (Y), lantanoid elements [lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.], and actinoid elements; group IV elements, including titanium (Ti), zirconium (Zr), and hafnium (Hf); group V elements, including vanadium (V), niobium (Nb), and tantalum (Ta); Group VI elements, including chromium (Cr), molybdenum (Mo), and tungsten (W); group VII elements, including manganese (Mn), technetium (Tc), and rhenium (Re); group VIII elements, including iron (Fe), ruthenium (Ru), and osmium (Os); group IX elements, including cobalt (Co), rhodium (Rh), and iridium (Ir); group X elements, including nickel (Ni), palladium (Pd), and platinum (Pt); group XI elements, including copper (Cu), silver (Ag), and gold (Au); group XII elements, including zinc (Zn), cadmium (Cd), and mercury (Hg); group XIII elements, including aluminum (Al), gallium (Ga), indium (In), and thallium (Tl); group XIV elements, including germanium (Ge), tin (Sn), and lead (Pb); group XV elements, including arsenic (As), antimony (Sb), and bismuth (Bi); and group XVI elements, including polonium (Po). Particularly, the central metal atom may be a group I or II element.

The metal complex compound according to an embodiment may have a structure in which the nitrogen or oxygen of the β-ketoimine ligand is coordinated to the central metal atom. Specifically, the metal complex compound according to an embodiment may be represented by the following Formula 4 or 5 wherein the central metal element is the Group II element strontium and $R^1$ and $R^2$ are each a methyl group:

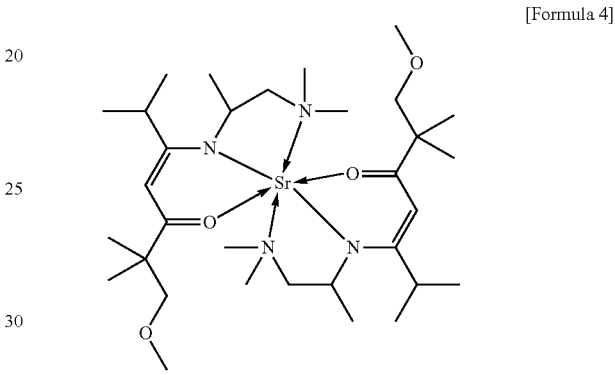

[Formula 4]

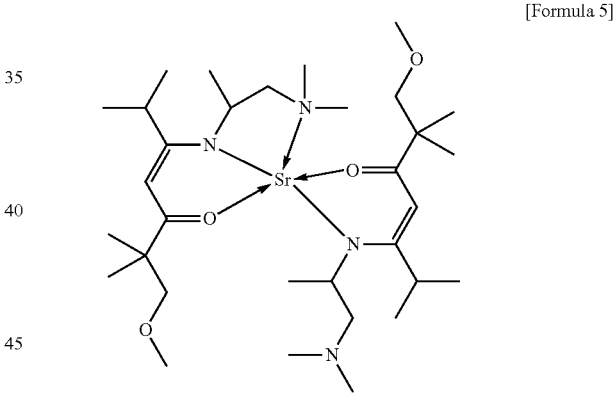

[Formula 5]

As shown in Formulas 4 and 5 above, the dimethylamino group of the N branched-chain of the β-ketoimine ligand may form a coordination bond by providing electrons to the central metal atom or may not be coordinated to the central metal atom, as indicated by the arrows. Formula 4 or 5 is only an exemplary form of the metal complex compound according to an embodiment, and the metal complex compound may vary. The scope according to an embodiment encompasses various forms of metal complex compounds regardless of coordination number or whether the dimethylamino group of the N chain is coordinated to the central metal atom.

Due to the β-ketoimine ligand, the above-described metal complex compound according to an embodiment may have a low melting point, excellent thermal stability and excellent solubility in an organic solvent, and thus may be suitable as a metal precursor in chemical vapor deposition or atomic layer deposition. Also, a metal complex compound including a group II element as its central metal may have more excellent thermal stability, and thus is useful for the formation of a thin film. Particularly, a metal complex compound having strontium as its central metal may be especially useful, because such a metal complex compound may be present in the liquid state at room temperature.

The metal complex compound according to an embodiment may be prepared by allowing the β-ketoimine ligand to react with an inorganic metal material containing a central metal atom, such as a halide, acetate, sulfate, carbonate or hydroxide, in the presence of a catalyst. Examples of the catalyst include base catalysts, such as sodium hydroxide (NaOH), diethylamine (HN(Et)$_2$), lithium (Li), lithium amide (LiNH$_2$), lithium methylate (CH$_3$OLi), sodium methylate (CH$_3$ONa), sodium amide (NaNH$_2$) or sodium (Na). In another implementation, the metal complex compound may be prepared by allowing the β-ketoimine ligand to react with a metal alkoxide or metal amide containing the central metal atom.

For a metal complex compound including a Group I or II element as its central metal, the metal complex compound can be prepared by allowing the β-ketoimine ligand to react directly with the group I or II metal. In a specific embodiment, the metal complex compound may be prepared by cooling a mixed solution of the group I or II metal and the β-ketoimine ligand in toluene and then allowing the mixed solution to react in the presence of ammonia gas. In another implementation, the metal complex compound may be prepared by dissolving a (bis[di(trimethylsilyl)amino]) metal and the β-ketoimine ligand and then allowing the solution to react.

Hereinafter, a composition for forming a thin film according to an embodiment will be described.

The composition for forming a thin film according to an embodiment includes the metal complex compound represented by Formula 3. The metal complex compound represented by Formula 3 includes the β-ketoimine ligand and may be used as a metal precursor in chemical vapor deposition process or atomic layer deposition process.

The composition for forming thin film may include an organic solvent. The metal complex compound represented by Formula 3 may be used intact or may be used after being dissolved in an organic solvent. The organic solvent may have a boiling point of 60° C. or higher and may be one or more of an acetate, such as ethyl acetate, butyl acetate, or methoxyethyl acetate; a ketone, such as methylbutyl ketone, methylisobutyl ketone, ethylbutyl ketone, dipropyl ketone, diisobutyl ketone, methyl n-amyl ketone, cyclohexanone, or methyl cyclohexanone; a hydrocarbon, such as hexane, cyclohexane, methyl cyclohexane, dimethyl cyclohexane, ethyl cyclohexane, heptane, octane, toluene, and xylene; an ether, such as tetrahydrofuran, tetrahydropyran, ethylene glycol dimethyl ether, diethylene glycol dimethyl ether, diethylene glycol dimethyl ether, dioxane, molpholine, and dibutyl ether; and an organic amide, such as 1-cyanopropane, 1-cyanobutane, 1-1-cyanohexane, cyanocylohexane, cyanobenzene, 1,3-dicyanopropane, 1,4-dicyanobutane, N-methyl-2-pyrrolidinone, N-ethyl-2-pyrrolidinone, or N-cyclohexyl-2-pyrrolidinone. The metal complex compound may be contained in the composition for forming a thin film at a concentration of 0.01-2.0 mol/L, and particularly 0.05-1.0 mol/L.

The composition for forming a thin film may further include, in addition to the metal complex compound, one or more other agents and/or precursors. Specific examples of the other agents and precursors include organic compounds, such as alcohol compounds, glycol compounds, β-diketone compounds, cyclopentadione compounds and organic amine compounds, and mixtures of such organic compounds with silicon (Si), boron (B), phosphorus (P) and a second metal. The second metal may, for example, be selected from among group I elements, including lithium (Li), sodium (Na), potassium (K), rubidium (Rb), and cesium (Cs); group II elements, including beryllium (Be), magnesium (Mg), calcium (Ca), barium (Ba), and strontium (Sr); group III elements, including scandium (Sc), yttrium (Y), lantanoid elements [lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.], and actinoid elements; group IV elements, including titanium (Ti), zirconium (Zr), and hafnium (Hf); group V elements, including vanadium (V), niobium (Nb), and tantalum (Ta); Group VI elements, including chromium (Cr), molybdenum (Mo), and tungsten (W); group VII elements, including manganese (Mn), technetium (Tc), and rhenium (Re); group VIII elements, including iron (Fe), ruthenium (Ru), and osmium (Os); group IX elements, including cobalt (Co), rhodium (Rh), and iridium (Ir); group X elements, including nickel (Ni), palladium (Pd), and platinum (Pt); group XI elements, including copper (Cu), silver (Ag), and gold (Au); group XII elements, including zinc (Zn), cadmium (Cd), and mercury (Hg); group XIII elements, including aluminum (Al), gallium (Ga), indium (In), and thallium (Tl); group XIV elements, including germanium (Ge), tin (Sn), and lead (Pb); group XV elements, including arsenic (As), antimony (Sb), and bismuth (Bi); and group XVI elements, including polonium (Po). For example, the other metal precursor may be a titanium precursor or a barium precursor.

Also, the composition for forming a thin film may contain a nucleophilic reagent. The nucleophilic reagent may impart stability to the metal complex compound according to an embodiment and to other precursors. Examples of the nucleophilic reagent include ethylene glycols, such as glyme, diglyme, triglyme, and tetraglyme; crown ethers, such as ethylene glycol ether, 18-crown-6, dicyclohexyl-18-crown-6,24-crown-8, dicyclohexyl-24-crown-8, and dibenzo-24-crown-8; polyamines, such as etheylene diamine, N,N'-tetramethylethyl diamine, diethylene triamine, triethylene teraamine, tetraethylene pentaamine, pentaethylene hexaamine, 1,1,4,7,7-pentamethyldiethylene triamine, 1,1,4,7,10,10-hexamethylethylene tetraamine, and triethoxytriethylene amine; cyclic polyamines, such as cyclam, and cyclen; and heterocyclic compounds, such as pyridine, pyrrolidine, piperidine, 1,4-dioxane, oxathiolane, oxazole, and thiazole. The nucleophilic reagent may be contained in an amount of 0.05-10 moles, and particularly 0.1-5.0 moles, based on one mole of the metal complex compound.

Hereinafter, a method for forming a thin film according to an embodiment will be described.

The thin film forming method according to an embodiment includes supplying a metal precursor including the metal complex compound above described, and forming a thin film on a workpiece by vaporizing the supplied metal precursor.

The metal complex compound used in thin film forming method according to an embodiment may have a high volatility and excellent thermal stability, and may be present in the liquid state at a process temperature, and thus may be formed into a thin film by a process such as chemical vapor deposition, molecular layer deposition (MLD) or atomic layer deposition (ALD). Examples of the chemical vapor deposition process include plasma enhanced chemical vapor deposition (PECVD), low-pressure chemical vapor deposition (LPCVD), direct liquid injection chemical vapor deposition (DLCVD), and cyclic chemical vapor deposition (CCVD).

More specifically, the supplying a metal precursor may include supplying a first raw material including the metal complex compound described above as a first metal precursor, and supplying a second raw material including a reactive gas. The first raw material and the second raw material may be supplied at the same time or sequentially.

The second raw material may contain a reactive gas to react with the first metal precursor. The reactive gas may be, for example, hydrogen ($H_2$), ammonia ($NH_3$), hydrazine ($NH_2NH_2$), or silane. In other implementations, steam ($H_2O$), oxygen ($O_2$), hydrogen peroxide ($H_2O_2$) or ozone ($O_3$) may be used as the reactive gas to deposit a metal oxide thin film.

Also, the supplying a metal precursor may further include supplying a third raw material including a second metal precursor. The third raw material may include a metal precursor different from the first metal precursor. For example, if the first metal precursor includes strontium and if the second raw material contains oxygen and if the second metal precursor includes titanium, a $SrTiO_3$ film may be formed.

Herein, the first to third raw materials may be supplied in the form of gas or steam. To vaporize the first metal precursor and the second metal precursor, these precursors may be bubbled with nitrogen gas, or thermal energy or plasma may be applied thereto. A carrier gas or diluent gas that is used to supply the first to third raw materials may be, for example, argon, nitrogen, helium, or a mixture thereof.

Then, the first raw material, the second raw material and the third material can react with each other to form a metal oxide film on a work piece such as a substrate.

Hereinafter, embodiments will be described in further detail with reference to examples and comparative examples. It is to be understood, however, that these examples are for illustrative purposes only and the scope is not limited thereto. Further, the Comparative Examples are set forth to highlight certain characteristics of certain embodiments, and are not to be construed as either limiting the scope of the invention as exemplified in the Examples or as necessarily being outside the scope of the invention in every respect.

Synthesis Example 1

Preparation of β-Ketoimine Ligand 1-1. Preparation of Intermediate Ether Ester Compound 1 mol of sodium hydride was added to the solvent dimethylformamide, and 1 mol of hydroxypivalic acid methyl ester was added thereto while the temperature of the solution did not exceed 30° C. The solution was stirred at room temperature for 90 minutes. Then, 1.2 mol of p-toluenesulfonic acid methyl ester was added to the solution while the temperature of the solution did not exceed 30° C. Then, a water/hexane mixture having the same mass as that of the dimethylformamide was added to the solution, which was then stirred, after which water was removed therefrom. The resulting organic material was concentrated, and the residue was fractionated at 700 Pa and 93° C., thereby obtaining the intermediate 3-methoxy-2,2-dimethylpropionic acid methyl ester at a yield of 55%.

1-2. Preparation of Intermediate β-Diketone Compound 2.5 mol of t-butoxy potassium was added to the solvent dimethylformamide, after which 1 mol of the intermediate ether ester compound obtained in Example 1-1 was added thereto while the temperature of the solution did not exceed 30° C. Then, the solution was stirred at room temperature for 40 minutes. Next, 1.5 mol of isopropylmethylketone was added to the solution while the temperature of the solution did not exceed 30° C., after which the solution was stirred at room temperature for 12 hours. Then, 36% hydrochloric acid corresponding to 30% of the mass of the dimethylformamide, water having the same mass as that of the dimethylformamide, and hexane having a mass 1.5 times that of the dimethylformamide were added to and mixed with the solution, after which water was removed therefrom. The resulting organic material was concentrated, and the residue was fractionated, thereby obtaining the intermediate 1-methoxy-2,2,6-trimethylheptane-3,5-dione at a yield of 56%.

1-3. Preparation of β-Ketoimine Ligand 1 mol of the intermediate β-diketone compound obtained in Example 1-2, 1.3 mol of 1-dimethylamino-2-propylamine, 36 wt % hydrochloric acid in an amount corresponding to 0.03 mol of hydrogen chloride, and butyl alcohol having a mass 3.5 times that of the β-diketone compound were added to a reaction flask and then refluxed for 11 hours. The reaction solution was concentrated, and the residue was fractionated by distillation under reduced pressure, thereby obtaining the desired product β-ketoimine ligand of the following Formula 6 at a yield of 74% from a fraction corresponding to 90 Pa and 110° C. FIG. 1 shows the $^1$H-NMR spectrum of the obtained β-ketoimine ligand in a benzene solution. Also, the molecular weight of the β-ketoimine ligand was measured by GC-MS.

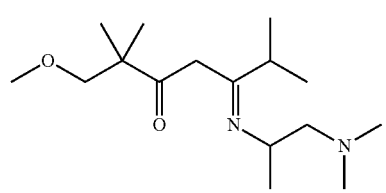

[Formula 6]

Synthesis Example 2

Preparation of β-Ketoimine Ligand 2-1. Preparation of Intermediate Ether Ester Compound 1 mol of sodium hydride was added to the solvent dimethylformamide, and 1 mol of hydroxypivalic acid methyl ester was added thereto while the temperature of the solution did not exceed 30° C. The solution was stirred at room temperature for 90 minutes. Then, 1.2 mol of p-toluenesulfonic acid ethyl ester was added to the solution while the temperature of the solution did not exceed 30° C. Then, a water/hexane mixture having the same mass as that of the dimethylformamide was added to and mixed with the solution, after which water was removed therefrom. The resulting organic material was concentrated, and the residue was fractionated at atmospheric pressure and 108~111° C., thereby obtaining the intermediate 3-ethoxy-2,2-dimethylpropionic acid methyl ester at a yield of 34%.

2-2. Preparation of Intermediate β-Diketone Compound 2.5 mol of t-butoxy potassium was added to the solvent dimethylformamide, after which 1 mol of the intermediate ether ester compound obtained in Example 2-1 was added thereto while the temperature of the solution did not exceed 30° C. Then, the solution was stirred at room temperature for 30 minutes. Next, 1.5 mol of isopropylmethylketone was added to the solution while the temperature of the solution did not exceed 30° C., after which the solution was stirred at room temperature for 12 hours. Then, 36% hydrochloric acid corresponding to 30% of the mass of the dimethylformamide, water having the same mass as that of the dimethylformamide, and hexane having a mass 1.5 times that of the dimethylformamide were added to and mixed with the solution, after which water was removed therefrom. The resulting organic material was concentrated, and the residue was fractionated, thereby obtaining the intermediate 1-ethoxy-2,2,6-trimethyl-heptane-3,5-dione at a yield of 63%.

Figure 2:
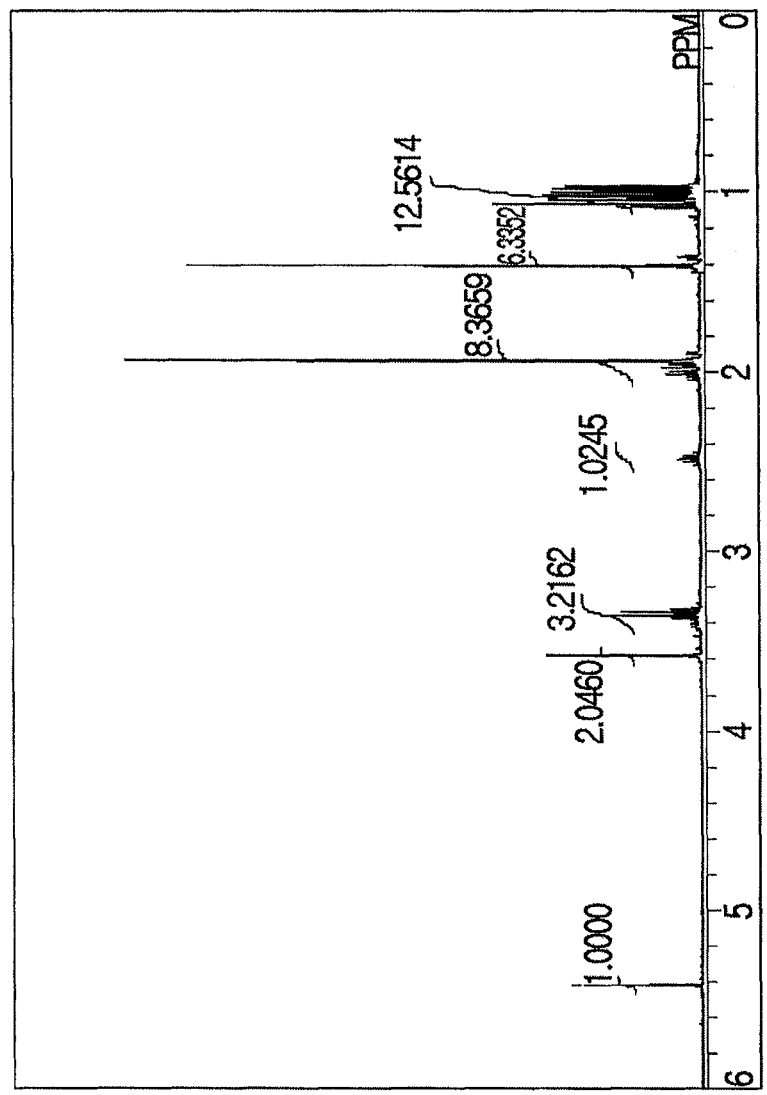
FIG. 2 illustrates the $^1$H-NMR spectrum of the β-ligand prepared in Synthesis Example 2.

2-3. Preparation of β-Ketoimine Compound 1 mol of the intermediate β-diketone compound obtained in Example 2-2, 1.3 mol of 1-dimethylamino-2-propylamine, 36 wt % hydrochloric acid in an amount corresponding to 0.03 mol of hydrogen chloride, and butyl alcohol having a mass 3.5 times that of the β-diketone compound were added to a reaction flask and then refluxed for 2 hours. The reaction solution was concentrated, and the residue was fractionated by distillation under reduced pressure, thereby obtaining the desired product β-ketoimine ligand of the following Formula 7 at a yield of 74% from a fraction corresponding to 40 Pa and 98° C. FIG. 2 shows the $^1$H-NMR spectrum of the obtained β-ketoimine ligand in a benzene solution. Also, the molecular weight of the β-ketoimine ligand was measured by GC-MS.

[Formula 7]

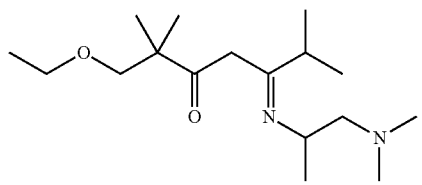

Synthesis Example 3

Preparation of β-Ketoimine Ligand 3-1. Preparation of Intermediate Ether Ester Compound 1 mol of sodium hydride was added to the solvent dimethylformamide, and 1 mol of hydroxypivalic acid methyl ester was added thereto while the temperature of the solution did not exceed 30° C. The solution was stirred at room temperature for 90 minutes. Then, 1.2 mol of p-toluenesulfonic acid ethyl ester was added to the solution while the temperature of the solution did not exceed 30° C. Then, a water/hexane mixture having the same mass as that of the dimethylformamide was added to and mixed with the solution, after which water was removed therefrom. The resulting organic material was concentrated, and the residue was fractionated under reduced pressure 76-79° C., thereby obtaining the intermediate 3-methoxy-2,2-dimethylpropionic acid methyl ester at a yield of 47%.

3-2. Preparation of Intermediate β-Diketone Compound 2.5 mol of t-butoxy potassium was added to the solvent dimethylformamide, after which 1 mol of the intermediate ether ester compound obtained in Example 3-1 was added thereto while the temperature of the solution did not exceed 30° C. Then, the solution was stirred at room temperature for 40 minutes. Next, 1.5 mol of 3-methyl-2-pentanone was added to the solution while the temperature of the solution did not exceed 30° C., after which the solution was stirred at room temperature for 12 hours. Then, 36% hydrochloric acid corresponding to 30% of the mass of the dimethylformamide, water having the same mass as that of the dimethylformamide, and hexane having a mass 1.5 times that of the dimethylformamide were added to and mixed with the solution, after which water was removed therefrom. The resulting organic material was concentrated, and the residue was fractionated, thereby obtaining the intermediate 1-methoxy-2,2,6-trimethylheptane-3,5-dione at a yield of 51%.

Figure 3:
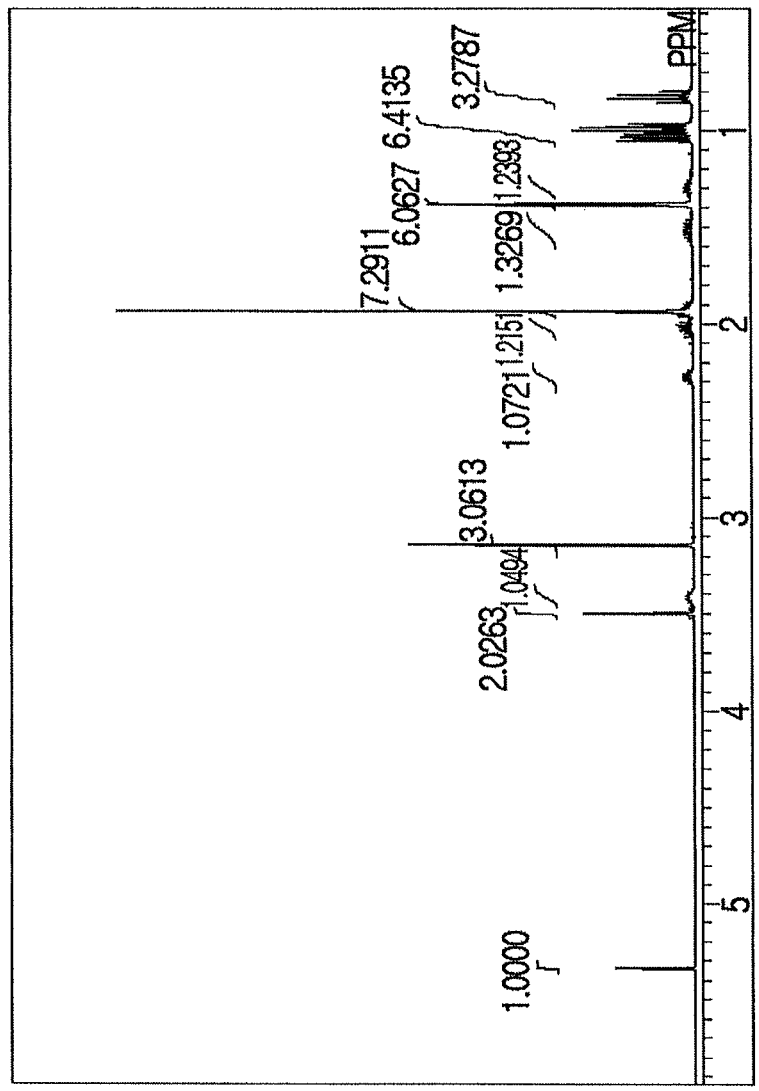
FIG. 3 illustrates the $^1$H-NMR spectrum of the β-ligand prepared in Synthesis Example 3.

3-3. Preparation of β-Ketoimine Compound 1 mol of the intermediate 3-diketone compound obtained in Example 3-2, 1.3 mol of 1-dimethylamino-2-propylamine, 36 wt % hydrochloric acid in an amount corresponding to 0.03 mol of hydrogen chloride, and butyl alcohol having a mass 3.5 times that of the β-diketone compound were added to a reaction flask and then refluxed for 3 hours. The reaction solution was concentrated, and the residue was fractionated by distillation under reduced pressure, thereby obtaining the desired product β-ketoimine ligand of the following Formula 8 at a yield of 68% from a fraction corresponding to 40 Pa and 103° C. FIG. 3 shows the $^1$H-NMR spectrum of the obtained β-ketoimine ligand in a benzene solution. Also, the molecular weight of the β-ketoimine ligand was measured by GC-MS.

[Formula 8]

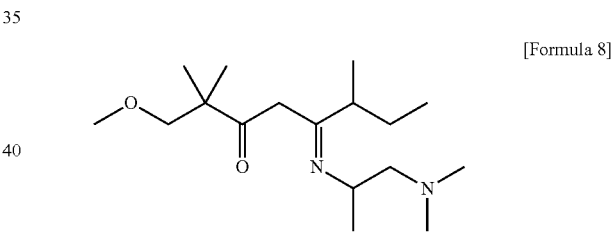

Synthesis Examples 4 to 7

Preparation of β-Ketoimine Ligand

Ligands represented by the following Formulas 9 to 12 were obtained in the same manner as Synthesis Examples 1 to 3, except that the β-diketone compound was allowed to react with an amine compound in the presence of hydrochloric acid, followed by purification by distillation. Also, the molecular weights of the obtained ligand compounds were measured by GC-MS.

<Formula 9>

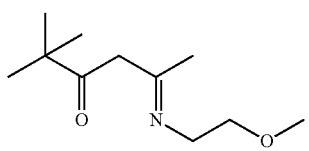

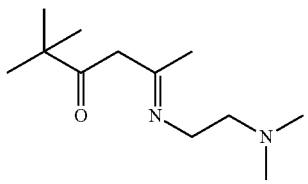
<Formula 10>

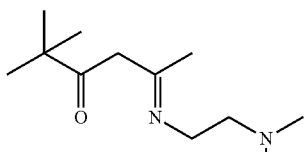
<Formula 11>

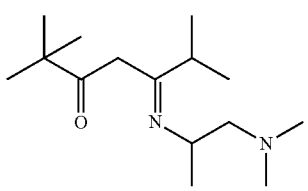
<Formula 12>

Synthesis Example 8

Preparation of β-Ketoimine Ligand 8-1. Preparation of Intermediate β-Diketone Compound 1.8 mol of sodium hydride was added to the solvent ethylene glycol dimethyl ether, and 1 mol of methyl 4-methoxybutanoate was added thereto and stirred at room temperature for 10 minutes. Then, 1.2 mol of t-butylmethylketone was added to the solution which was then stirred at 92° C. for 19 hours. Then, the solution was cooled to room temperature and quenched in 36% hydrochloric acid, after which water and dimethylether were added to and mixed with the solution, and water was removed therefrom. The resulting organic material was washed with 1 wt % sodium hydroxide and then with saturated saline and concentrated, and the residue was fractionated, thereby obtaining the intermediate 8-methoxy-2,2-dimethyloctan-3,5-dione at a yield of 14%.

8-2. Preparation of β-Ketoimine Compound 1 mol of the intermediate β-diketone compound obtained in Example 8-1, 1.3 mol of N,N-dimethyl-1,3-propanediamine, 36 wt % hydrochloric acid in an amount corresponding to 0.03 mol of hydrogen chloride, and butyl alcohol having a mass 3.5 times that of the β-diketone compound were added to a reaction flask and then refluxed for 5 hours. The reaction solution was concentrated, and the residue was fractionated by distillation under reduced pressure, thereby obtaining a β-ketoimine ligand of the following Formula 13 at a yield of 55% from a fraction corresponding to 40 Pa and 120° C. The molecular weight of the obtained β-ketoimine ligand was measured by GC-MS.

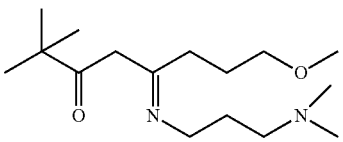
<Formula 13>

Synthesis Example 9

Preparation of β-Ketoimine Ligand

The intermediate β-diketone compound was prepared in the same manner as Synthesis Example 1. Then, 1 mol of the β-diketone compound, 1.2 mol of 1-methoxy-2-propylamine, 36 wt % hydrochloric acid in an amount corresponding to 0.03 mol of hydrogen chloride, and butyl alcohol having a mass 3.5 times that of the β-diketone compound were added to a reaction flask and then refluxed for 7 hours. The reaction solution was concentrated, and the residue was fractionated by distillation under reduced pressure, thereby obtaining a β-ketoimine ligand of the following Formula 14 at a yield of 56% from a fraction corresponding to 75 Pa and 118° C. The molecular weight of the obtained β-ketoimine ligand was measured by GC-MS.

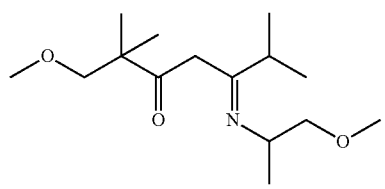
<Formula 14>

Synthesis Example 10

Preparation of β-Ketoimine Ligand

The intermediate β-diketone compound was prepared in the same manner as Synthesis Example 1. Then, 1 mol of the β-diketone compound, 1.5 mol of N,N-dimethylethyleneamine, 36 wt % hydrochloric acid in an amount corresponding to 0.03 mol of hydrogen chloride, and butyl alcohol having a mass 3.5 times that of the β-diketone compound were added to a reaction flask and then refluxed for 3 hours. The reaction solution was concentrated, and the residue was fractionated by distillation under reduced pressure, thereby obtaining a β-ketoimine ligand of the following Formula 15 at a yield of 58% from a fraction corresponding to 40 Pa and 103° C. The molecular weight of the obtained β-ketoimine ligand was measured by GC-MS.

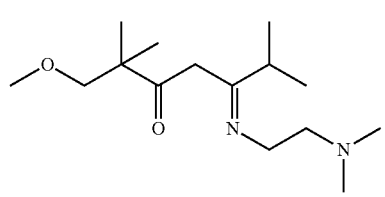
<Formula 15>

Synthesis Example 11

11-1. Preparation of Intermediate Lactone Compound 1 mol of sodium hydride was dissolved in tetrahydrofuran and refluxed under argon. 1 mol of γ-butyrolactone and 3 mol of iodomethane were added thereto. The reaction solution was cooled to 0° C., after which water was added in the same amount as that of the tetrahydrofuran, and the temperature of the solution was elevated to room temperature. Then, diethyl ether was added thereto in an amount 0.75 times that of the tetrahydrofuran, after which water was removed, and the remaining material was dehydrated with magnesium sulfate. The resulting organic material was fractionated, thereby obtaining the intermediate α,α-dimethyl-γ-butyrolactone at a yield of 32%.

11-2. Preparation of Intermediate Ether Ester Compound 1 mol of the above-prepared lactone compound, 2 mol of ortho-formic acid methyl and 0.06 mol of sulfuric acid were added to methanol and mixed under argon at 50° C. for 6 hours. The reaction solution was cooled to room temperature, after which hexane having a mass 0.75 times that of the methanol was added thereto, and methanol was removed therefrom. The remaining material was dried with magnesium sulfate to remove hexane and concentrated, and the residue was fractionated, thereby obtaining the intermediate 4-methoxy-2,2-dimethylbutanoic acid methyl ester at a yield of 44%.

11-3. Preparation of Intermediate β-Diketone Compound 2.5 mol of potassium t-butoxide was dissolved in dimethylformamide, and 1 mol of the intermediate 4-methoxy-2,2-dimethylbutanoic acid methyl ester obtained in Synthesis Example 11-2 was added thereto while the temperature of the solution did not exceed 30° C., after which the solution was stirred in an argon atmosphere at a room temperature for 40 minutes. Then, 1.5 mol of isopropylmethylketone was added thereto while the temperature of the solution did not exceed 30° C., after which the solution was stirred at 50° C. for 13 hours. Then, 36% hydrochloric acid was added to the solution in an amount of 8 wt % based on the weight of the dimethylformamide, after which water having the same mass as that of the dimethylformamide, and hexane having a mass 0.5 times that of the dimethylformamide were added to and mixed with the solution, and water removed therefrom. The resulting organic material was dried with magnesium sulfate and concentrated, and the residue was fractionated by distillation under reduced pressure, thereby obtaining the intermediate 8-methoxy-2,6,6-trimethyloctan-3,5-dione at a yield of 26%.

11-4. Preparation of β-Ketoimine Compound 1 mol of the intermediate β-diketone compound obtained in Synthesis Example 11-3, 1.3 mol of 1-dimethylamino-2-propylamine, 36 wt % hydrochloric acid in an amount corresponding to 0.03 mol of hydrogen chloride, and butyl alcohol having a mass 3.5 times that of the β-diketone compound were added to a reaction flask and then refluxed for 4 hours. The reaction solution was concentrated, and the residue was fractionated by distillation under reduced pressure, thereby obtaining a β-ketoimine ligand of the following Formula 16 at a yield of 73% from a fraction corresponding to 40 Pa and 98° C. The molecular weight of the obtained β-ketoimine ligand was measured by GC-MS.

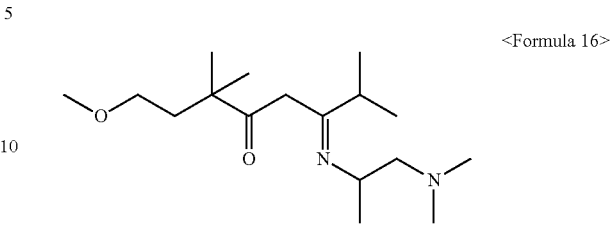

<Formula 16>

Example 1

Preparation of Strontium Complex Compound

In a reaction flask, 2 mol of the β-ketoimine ligand represented by above Formula 6 obtained in Synthesis Example 1, 1 mol of $Sr[N(SiMe_3)_2]_2(CH_3OCH_2CH_2OCH_3)_2$, and dehydrated toluene in an amount of 20 mol ratio based on mol of $Sr[N(SiMe_3)_2]_2(CH_3OCH_2CH_2OCH_3)_2$ were stirred at room temperature for 1 day, and then the solution was evaporated under reduced pressure to remove the solvent. Then, unreacted particles were removed at 160° C. and 40 Pa, after which the residue was distilled under reduced pressure, thereby obtaining a strontium complex compound as a pale yellow liquid at a yield of 70% from a fraction corresponding to 40 Pa and 205° C. The preparation and purification operations were all performed in a dry argon atmosphere.

Figure 4:
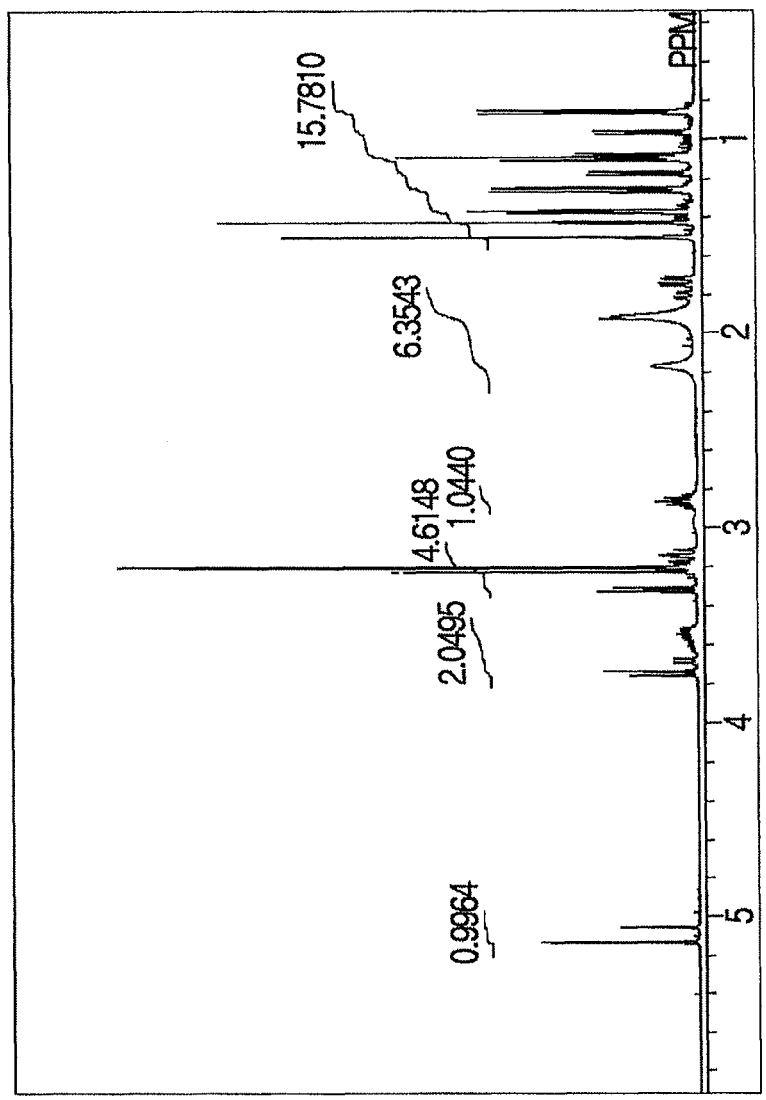
FIG. 4 illustrates the $^1$H-NMR spectrum of the metal complex compound prepared in Example 1.

For the obtained pale yellow liquid, the measurement of the $^1$H-NMR spectrum in a benzene solution, the measurement of the Sr content by ICP spectroscopy, the measurement of C, N and H by a CHN analyzer, and the measurement of molecular weight by mass spectroscopy were performed. FIG. 4 shows the $^1$H-NMR spectrum of the pale yellow liquid. The results of elementary analysis and measurement of molecular weight are as follows:

Sr, 13.1 wt %, C, 59.2 wt %, N, 9.1 wt %, H, 10.1 wt %; molecular weight: 655.

Example 2

Preparation of Strontium Complex Compound

In a reaction flask, 2 mol of the β-ketoimine ligand of Formula 7 obtained in Synthesis Example 2, 1 mol of strontium, and dehydrated toluene having a mass two times that of the β-ketoimine ligand were added, cooled to −40° C., and then stirred −40° C. for 3 hours while ammonia gas was blown therein. Then, the temperature of the reaction solution was elevated slowly to room temperature, after undissolved material was filtered out, and the reaction solution was concentrated. The residue was distilled under reduced pressure, thereby obtaining a strontium complex compound as a yellow liquid at a yield of 69% from a fraction corresponding to 33 Pa and 203° C. The preparation and purification operations were all performed in a dry argon atmosphere.

Figure 5:
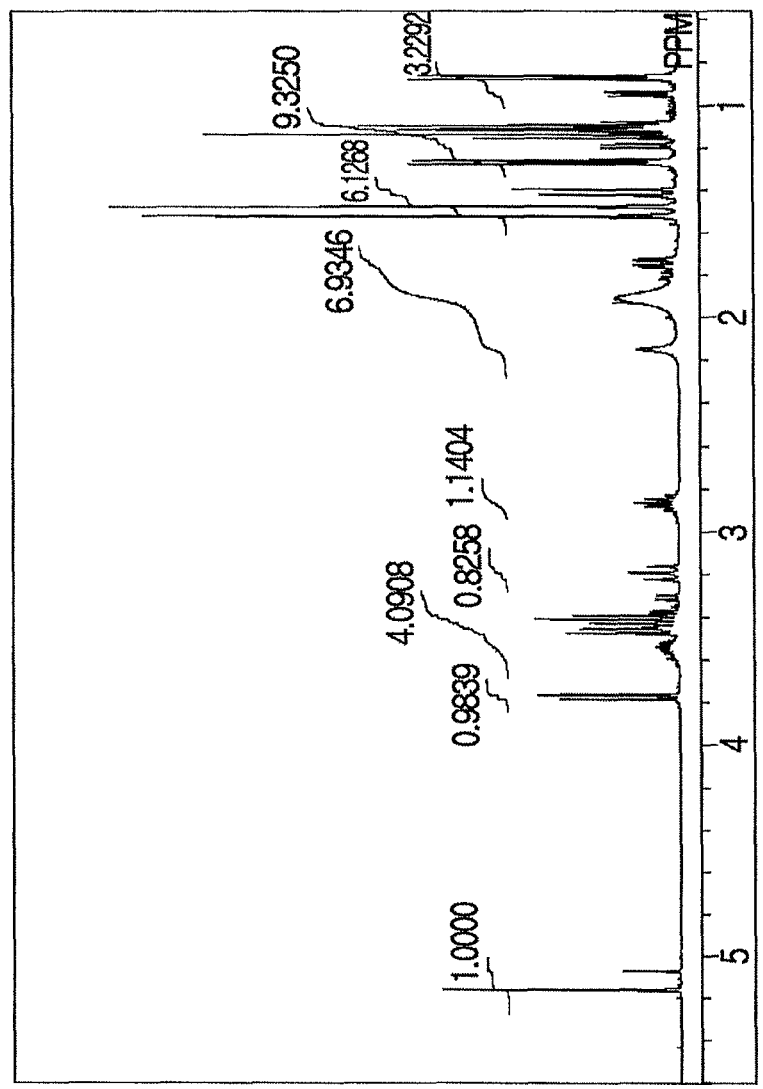
FIG. 5 illustrates the $^1$H-NMR spectrum of the metal complex compound prepared in Example 2.

For the obtained yellow liquid, the measurement of the $^1$H-NMR spectrum in a benzene solution, the measurement of the Sr content by ICP spectroscopy, the measurement of C, N and H by a CHN analyzer, and the measurement of molecular weight by mass spectroscopy were performed. FIG. 5 shows the $^1$H-NMR spectrum of the strontium complex compound obtained in Example 2. The results of elementary analysis and measurement of molecular weight are as follows:

Sr, 12.8 wt %, C, 59.8 wt %, N, 8.2 wt %, H, 9.9 wt %; molecular weight: 683.

Example 3

Preparation of Strontium Complex Compound

In a reaction flask, 2 mol of the β-ketoimine ligand of Formula 8 obtained in Synthesis Example 3, 1 mol of strontium, and dehydrated toluene having a mass two times that of the β-ketoimine ligand were added, cooled to −40° C., and then stirred −40° C. for 3 hours while ammonia gas was blown therein. Then, the temperature of the reaction solution was elevated slowly to room temperature and filtered, and the filtrate was concentrated. The residue was distilled under reduced pressure, thereby obtaining a strontium complex compound as a yellow liquid at a yield of 68% from a fraction corresponding to 34 Pa and 208° C. The preparation and purification operations were all performed in a dry argon atmosphere.

Figure 6:
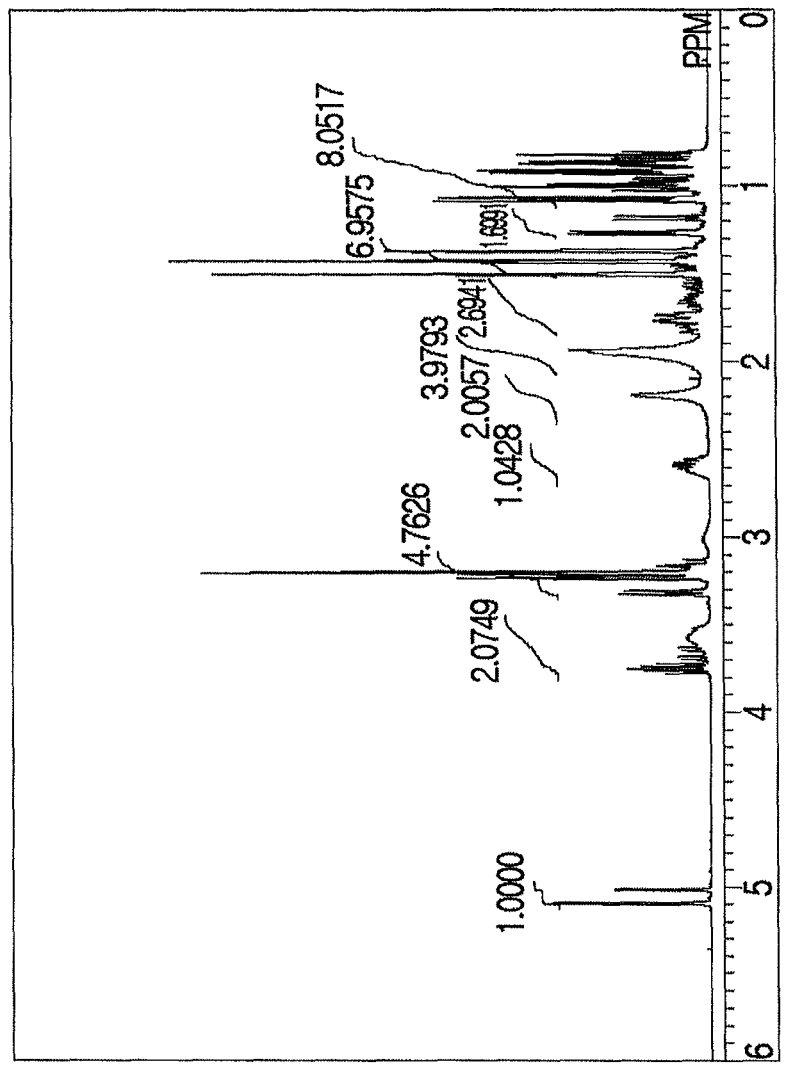
FIG. 6 illustrates the $^1$H-NMR spectrum of the metal complex compound prepared in Example 3.

For the obtained yellow liquid, the measurement of the $^1$H-NMR spectrum in a benzene solution, the measurement of the Sr content by ICP spectroscopy, the measurement of C, N and H by a CHN analyzer, and the measurement of molecular weight by mass spectroscopy were performed. FIG. 6 shows the $^1$H-NMR spectrum of the strontium complex compound obtained in Example 3. The results of elementary analysis and measurement of molecular weight are as follows:

Sr, 13.4 wt %, C, 59.3 wt %, N, 8.1 wt %, H, 9.9 wt %; molecular weight: 683.

Comparative Examples 1 to 8

Preparation of Strontium Complex Compounds

Strontium complex compounds of Comparative Examples 1 to 8 were prepared using the β-ketoimine ligands, obtained in Synthesis Examples 4 to 11, in the same manner as Example 1. Purification of the strontium complex compounds of Comparative Examples 3, 4, 5, 6 and 8, which could be distilled, was carried out at a pressure of 30-50 Pa and a temperature of 200~220° C. For the complex compounds of Comparative Examples 1, 2 and 7, which could not be purified by distillation due to low thermal stability, only low-melting-point impurities were removed under the conditions of 30 Pa and 160° C. The strontium complex compounds of Comparative Examples 1 to 8 were analyzed in the same manner as Examples 1 to 3, thereby determining the chemical structures thereof. The results of the analysis are shown in Table 1 below.

TABLE 1

| Comparative Examples | Ligand | Elementary analysis by CHN Analyzer 1H-NMR (C6D6 solvent) | Sr content (%) | Molecular weight |
|---|---|---|---|---|
| 1 | Synthesis Example 4 | C: 54.0 wt %, N: 5.6 wt % H: 8.3 wt % 1.41 (s, 18), 1.80 (s, 6), 3.17-3.18 (m, 10), 3.41 (t, 4), 5.11 (s, 2) | 18.3 | 484 |
| 2 | Synthesis Example 5 | C: 56.5 wt % N: 11.1 wt %, H: 9.2 wt % 1.39 (s, 18), 1.77 (s, 6), 1.88 (br, 10), 2.96 (t, 4), 5.17 (s, 2) | 17.0 | 510 |
| 3 | Synthesis Example 6 | C: 58.0 wt %, N: 10.5 wt %, H: 9.5 wt % 0.93 (d, 6), 1.37 (s, 2), 1.40 (s, 18), 1.76 (br, 6), 1.83 (s, 6), 1.95 (br, 6), 3.31 (t, 2), 3.39-3.41 (m, 2), 5.11 (s, 2) | 16.5 | 538 |
| 4 | Synthesis Example 7 | C: 60.2 wt %, N: 9.3 wt %, H: 9.8 wt % 0.84-0.86 (d, 3), 1.10-1.11 (d, 3), 1.24-1.27 (d, 3), 1.40 (s, 9), 1.68-1.76 (m, 4), 1.97 (br, 3), 2.82-2.87 (m, 1), 3.23 (t, 1), 3.49-3.54 (m, 1) | 14.7 | 594 |
| 5 | Synthesis Example 8 | C: 57.0 wt %, N: 9.1 wt %, H: 9.3 wt % C 1.33-1.43 (m, 2), 1.45(s, 9), 1.83-1.90 (m, 2), 1.96 (br, 3), 2.12 (br, 3), 2.17 (br, 1), 2.29 (br, 1), 2.34 (t, 2), 3.15 (s, 3), 3.27 (t, 2), 3.47-3.57 (br, 2), 5.13 (s, 1) | 13.4 | 654 |
| 6 | Synthesis Example 9 | C: 57.3 wt %, N: 4.5 wt %, H: 8.9 wt % 1.05-1.19 (m, 9), 1.38-1.49 (d, 6) 2.73-2.90 (m, 3), 3.13 (s, 3), 3.24 (s, 3), 3.45-3.68 (m, 3), 5.10-5.14 (s, 1) | 13.9 | 628 |
| 7 | Synthesis Example 10 | C: 57.8 wt %, N: 9.2 wt %, H: 9.5 wt % 1.13-1.15 (d, 6), 1.45 (s, 6), 1.97 (s, 6), 2.25 (m, 2), 2.83 (m, 1), 3.13 (m, 2), 3.20 (s, 3), 3.51 (m, 2), 5.17 (s, 1) | 14.0 | 626 |
| 8 | Synthesis Example 11 | C: 59.8 wt %, N: 8.2 wt %, H: 9.8 wt % 1.03-1.05 (d, 3), 1.10-1.12 (d, 3), 1.19-1.21 (d, 3), 1.35 (s, 3), 1.40 (s, 3), 2.04 (br, 6), 2.14 (s, 2), 2.20-2.23 (m, 1), 2.84-2.87 (m, 1), 3.15 (s, 3), 3.40-3.57 (m, 4), 5.03 (s, 1) | 12.8 | 683 |

The strontium complex compounds obtained in Examples 1 to 3 and Comparative Examples 1 to 8 can be represented by the following Formula 17:

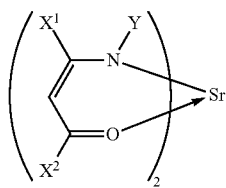

<Formula 17> wherein $X^1$, $X^2$ and Y each represents a group introduced by the β-ketoimine ligand.

Test Example 1

Evaluation of Melting Point (Liquefying Point)

The melting points of the strontium complex compounds obtained in Examples 1 to 3 were measured by visual observation. The results of the measurement are shown in Table 2 below.

TABLE 2

|  | Melting (° C.) |
|---|---|
| Example 1 | Liquefied at 25° C. |
| Example 2 | Liquefied at 25° C. |
| Example 3 | Liquefied at 25° C. |
| Comparative Example 1 | 140~141 |
| Comparative Example 2 | 185~186 |
| Comparative Example 3 | 155~156 |
| Comparative Example 4 | 139~140 |
| Comparative Example 5 | 111~112 |
| Comparative Example 6 | 80~85 |
| Comparative Example 7 | 70~80 |
| Comparative Example 8 | 138~139 |

As can be seen in Table 2 above, the strontium complex compounds of Examples 1 to 3 including the β-ketoimine ligand according to embodiments, were liquefied at 25° C. On the other hand, the strontium complex compounds of Comparative Examples 1 to 8 were liquefied at a temperature of 70° C. or higher. Accordingly, it can be seen that a complex compound having a low melting point can be synthesized using the β-ketoimine ligand according to the present embodiments and is suitable for the formation of a thin film.

Test Example 2

Evaluation of Solubility in Organic Solvent

For the strontium complex compounds of Examples 1 to 3 and Comparative Examples 2 to 8, the solubilities of the complex compounds in ethyl cyclohexane, diethyl glycol dimethyl ether and toluene were evaluated. The evaluation was performed by adding 0.1-0.7 mol of each of the strontium complex compounds to 1000 ml of each of the organic solvents, sealing the mixtures, allowing the mixtures to stand for 24 hours, and visually observing whether a solid occurred in the mixtures. Table 3 below shows the concentration of the strontium complex compound in the transparent liquid in which no solid was present. In Table 3, the case in which the complex compound was dissolved at a concentration of less than 0.1 mol was indicated as "x".

TABLE 3

|  | Ethyl cyclohexane | Diethylene glycol dimethyl ether | Toluene |
|---|---|---|---|
| Example 1 | 0.7 mol | 0.7 mol | 0.7 mol |
| Example 2 | 0.6 mol | 0.7 mol | 0.7 mol |
| Example 3 | 0.7 mol | 0.7 mol | 0.7 mol |
| Comparative Example 2 | x | 0.3 mol | 0.3 mol |
| Comparative Example 3 | 0.1 mol | 0.7 mol | 0.5 mol |
| Comparative Example 4 | 0.3 mol | 0.4 mol | 0.7 mol |
| Comparative Example 5 | x | 0.4 mol | 0.1 mol |
| Comparative Example 6 | 0.5 mol | 0.4 mol | 0.4 mol |
| Comparative Example 7 | 0.3 mol | 0.2 mol | 0.3 mol |
| Comparative Example 8 | x | x | 0.1 mol |

As can be seen in Table 3 above, the complex compounds of Examples 1 to 3 including the β-ketoimine ligand were clearly dissolved in all the three organic solvents at a concentration of 0.7 mol/l or less, indicating that the complex compounds had good solubility. On the other hand, some of the complex compounds of the Comparative Examples were not dissolved even at a concentration of 0.1 mol/l, and the solubility thereof was generally inferior to that of the complex compounds of the Examples.

The complex compound having good solubility in the organic solvent has a low possibility of solid precipitation even if a solution supply method is used to form a thin film by chemical vapor deposition or atomic layer deposition. In addition, in the case of this complex compound, the change in the film formation rate with time and the possibility of deterioration in the film quality are reduced.

Test Example 3

Evaluation of Thermal Stability

The strontium complex compounds of Examples 1 to 3 and Comparative Examples 5 to 8 were measured for thermal stability by TGA and DSC. The TGA measurement was carried out under the following conditions: dry argon flow rate: 100 ml/min; heating rate: 10° C./min; and a sample amount of 7-12 mg. The DSC measurement was carried out by injecting a sample into a closed metal container in a glove box in a dry argon atmosphere and heating the sample container at a rate of 10° C./min, in which the amount of the sample was 1-4 mg. In the TGA measurement, sampling and measurement were carried out in the glove box in the dry argon atmosphere. The remaining amount at 400° C. in TGA and the decomposition peak top temperature in DSC are shown in Table 4 below.

TABLE 4

|  | Remaining amount (wt % at 400° C. | Decomposition peak top temperature (° C.) |
|---|---|---|
| Example 1 | 0.61 | 382.4 |
| Example 2 | 1.40 | 360.7 |
| Example 3 | 0.87 | 393.2 |
| Comparative Example 5 | 26.2 | 336.8 |
| Comparative Example 6 | 3.7 | 363.0 |
| Comparative Example 7 | 10.2 | 337.5 |

TABLE 4-continued

| | Remaining amount (wt % at 400° C.) | Decomposition peak top temperature (° C.) |
|---|---|---|
| Comparative Example 8 | 3.97 | 368.2 |

As can be seen in Table 4 above, the strontium complex compounds of Examples 1 to 3 showed decomposition peak top temperatures higher than the complex compounds of Comparative Examples, suggesting that the strontium complex compounds of Examples 1 to 3 have good thermal stability.

As described above, it can be seen that the metal complex compound comprising the β-ketoimine ligand has a low melting point, excellent thermal stability and excellent solubility in an organic solvent, and thus is suitable for the formation of a thin film.

By way of summation and review, it is desirable for precursors for an MOCVD process to have a sufficiently high vapor pressure at low temperature, to possess a low melting point and to have sufficient thermal stability during heating for vaporization. Also, it is desirable for the precursors to have a temperature window at which they may decompose rapidly at higher temperatures without causing the decomposition of organic materials or the like. Metal complex compounds that are used as precursors for MOCVD to fabricate metal oxide thin films may typically include halogen compounds containing chlorine, bromine or iodine, nitric oxides, alkoxides, β-diketonate compounds and the like. These precursors have advantages and disadvantages according to their ligands, and they generally have high melting points and may be thermally unstable.

Accordingly, in order to fabricate good quality thin films, the development of MOCVD precursors which have low melting points and improved volatility and thermal stability is required.

Embodiments disclosed herein advance the art by providing a β-ketoimine ligand capable of forming a metal complex compound that has a low melting point, excellent thermal stability and excellent solubility in an organic solvent, and thus is suitable for the formation of thin films.

Embodiments further provide a method for preparing a β-ketoimine ligand capable of providing a metal complex compound that has a low melting point, excellent thermal stability and excellent solubility in an organic solvent, and thus is suitable for the formation of thin films.

Embodiments further provide a metal complex compound containing a β-ketoimine ligand, in which the metal complex compound has a low melting point, excellent thermal stability and excellent solubility in an organic solvent, and thus is suitable for the formation of thin films.

Embodiments further provide a method of forming a thin film using a metal complex compound containing a β-ketoimine ligand, in which the metal complex compound has a low melting point, excellent thermal stability and excellent solubility in an organic solvent, and thus is suitable for the formation of thin films.

Example embodiments have been disclosed herein, and although specific terms are employed, they are used and are to be interpreted in a generic and descriptive sense only and not for purpose of limitation. Accordingly, it will be understood by those of skill in the art that various changes in form and details may be made without departing from the spirit and scope as set forth in the following claims.

What is claimed is:

1. A β-ketoimine compound represented by the following Formula 1:

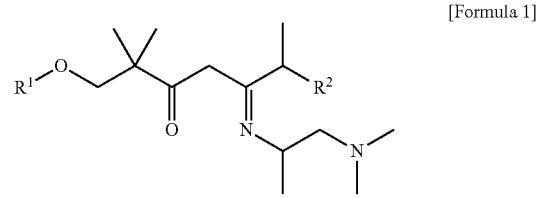

[Formula 1]

wherein $R^1$ and $R^2$ are each independently a $C_1$-$C_5$ alkyl group.

2. The β-ketoimine compound as claimed in claim 1, wherein $R^1$ and $R^2$ are each independently a methyl group or an ethyl group.

* * * * *